United States Patent
Schlitter et al.

(10) Patent No.: US 7,807,603 B2
(45) Date of Patent: Oct. 5, 2010

(54) CATALYST EXTRUDATES BASED ON COPPER OXIDE AND THEIR USE FOR HYDROGENATING CARBONYL COMPOUNDS

(75) Inventors: Stephan Schlitter, Limburgerhof (DE); Olga Schubert, Ludwigshafen (DE); Michael Hesse, Worms (DE); Sabine Borchers, Erlenbach bei Kandel (DE); Markus Roesch, Dienheim (DE); Rolf Pinkos, Bad Duerkheim (DE); Alexander Weck, Freinsheim (DE); Gunther Windecker, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 617 days.

(21) Appl. No.: 10/580,950

(22) PCT Filed: Dec. 4, 2004

(86) PCT No.: PCT/EP2004/013809
§ 371 (c)(1),
(2), (4) Date: May 30, 2006

(87) PCT Pub. No.: WO2005/058491
PCT Pub. Date: Jun. 30, 2005

(65) Prior Publication Data
US 2007/0117719 A1    May 24, 2007

(30) Foreign Application Priority Data
Dec. 9, 2003    (DE) ................................. 103 57 717

(51) Int. Cl.
*B01J 23/00* (2006.01)
*B01J 21/00* (2006.01)
*B01J 20/00* (2006.01)
*B01J 29/00* (2006.01)
*B01J 37/00* (2006.01)

(52) U.S. Cl. .................. 502/346; 502/263; 502/324; 502/345; 502/349; 502/350; 502/351; 502/355; 502/407; 502/415; 502/439

(58) Field of Classification Search ................ 502/244, 502/324, 331, 345, 346, 349, 350, 355, 415, 502/439, 263, 351, 407
See application file for complete search history.

(56) References Cited

U.S. PATENT DOCUMENTS 3,271,324 A * 9/1966 Hirschler, Jr. et al. ....... 502/331

(Continued)

FOREIGN PATENT DOCUMENTS

DE    2 332 906    4/1974

(Continued)

OTHER PUBLICATIONS

Mueller, Steffen Peter et al., "Extrusion of Cu/ZnO catalysts for the single-stage gas-phase processing of dimethyl maleate to tetrahydrofuran", Journal of Catalysis, vol. 218, pp. 419-426, 2003.

*Primary Examiner*—Cam N Nguyen
(74) *Attorney, Agent, or Firm*—Oblon, Spivak, McClelland, Maier & Neustadt, L.L.P.

(57) ABSTRACT

The invention relates to a catalyst provided in the form of an extrudate, which contains 5 to 85% by weight of copper oxide and comprises, in the active material and as binders, the same oxidic carrier material. The invention also relates to the use of the catalyst for hydrogenating carbonyl compounds.

20 Claims, 1 Drawing Sheet

U.S. PATENT DOCUMENTS

Figure 1:
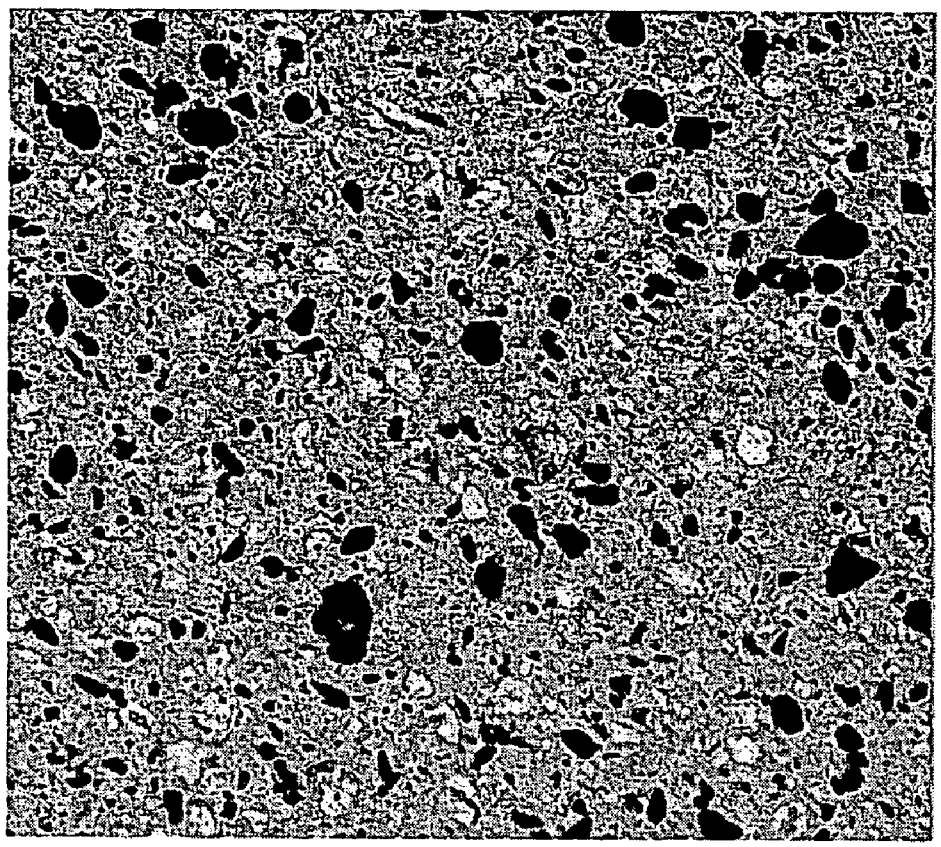

| | | | |
|---|---|---|---|
| 3,438,721 A * | 4/1969 | Innes | 423/213.2 |
| 3,447,893 A * | 6/1969 | Hirschler, Jr. et al. | 423/213.2 |
| 3,661,806 A * | 5/1972 | Briggs et al. | 502/313 |
| 3,759,845 A * | 9/1973 | Rudoff et al. | 502/324 |
| 3,839,224 A * | 10/1974 | Yonehara et al. | 502/66 |
| 3,914,390 A * | 10/1975 | Kudo et al. | 423/351 |
| 3,928,238 A * | 12/1975 | Koberstein et al. | 502/241 |
| 3,988,263 A * | 10/1976 | Hansford | 502/337 |
| 4,165,546 A * | 8/1979 | Philipson et al. | 4/262 |
| 4,174,355 A * | 11/1979 | Patel et al. | 585/843 |
| 4,423,155 A | 12/1983 | Bell et al. | |
| 4,601,998 A * | 7/1986 | Oleck et al. | 502/318 |
| 4,666,879 A | 5/1987 | Kelly et al. | |
| 4,871,710 A * | 10/1989 | Denny et al. | 502/414 |
| 4,977,123 A * | 12/1990 | Flytzani-Stephanopoulos et al. | 502/84 |
| 4,996,181 A * | 2/1991 | Denny et al. | 502/414 |
| 5,155,086 A * | 10/1992 | Thakur et al. | 502/342 |
| 5,218,003 A * | 6/1993 | Lewnard et al. | 518/700 |
| 5,347,021 A * | 9/1994 | Taylor et al. | 549/325 |
| 6,338,830 B1 * | 1/2002 | Moskovitz et al. | 423/210 |
| 6,455,464 B1 * | 9/2002 | Chen | 502/346 |
| 6,664,207 B2 * | 12/2003 | Yao et al. | 502/61 |
| 6,689,713 B1 * | 2/2004 | Zhao et al. | 502/345 |
| 6,730,800 B2 * | 5/2004 | Fischer et al. | 549/507 |
| 6,784,135 B2 * | 8/2004 | Scholten et al. | 502/245 |
| 6,831,182 B2 * | 12/2004 | Borchert et al. | 549/508 |
| 6,852,298 B2 * | 2/2005 | Kelkar et al. | 423/239.1 |
| 6,913,739 B2 * | 7/2005 | Shore et al. | 423/247 |
| 6,916,457 B2 * | 7/2005 | Chen | 423/219 |
| 6,919,066 B2 * | 7/2005 | Holzle et al. | 423/648.1 |
| 6,926,880 B2 * | 8/2005 | Holzle et al. | 423/648.1 |
| 6,958,404 B2 * | 10/2005 | Borchert et al. | 549/325 |
| 7,033,972 B2 * | 4/2006 | Shikada et al. | 502/307 |
| 7,217,679 B2 * | 5/2007 | Borchert et al. | 502/304 |

FOREIGN PATENT DOCUMENTS

| | | |
|---|---|---|
| EP | 1000658 A2 * | 5/2000 |
| EP | 1 228 803 | 8/2002 |
| WO | 97/34694 | 9/1997 |

* cited by examiner

CATALYST EXTRUDATES BASED ON COPPER OXIDE AND THEIR USE FOR HYDROGENATING CARBONYL COMPOUNDS

The present invention relates to shaped catalyst bodies, preferably in the form of extrudates, which are based on an active composition comprising copper oxide and an oxidic support material together with a binder and their use in processes for the hydrogenation of carbonyl compounds.

Copper catalysts have a wide range of uses in the chemical industry. Supported copper catalysts are a suitable choice for, in particular, the hydrogenation of carbonyl compounds such as carboxylic esters and anhydrides, of aldehydes or nitro compounds. These catalysts are usually produced and used in the form of pellets as shaped bodies.

One possible way of improving these catalysts, for example in respect of their selectivity in respect of subsequent reactions, is to optimize the geometry of the shaped bodies and the porosity for the particular application. However, there are limits to this optimization of catalyst pellets because small, porous pellets either no longer have a satisfactory mechanical strength or they become disproportionately expensive to produce.

It is therefore an object of the invention to find an optimized catalyst system which alleviates the abovementioned disadvantages of the catalyst pellets according to the prior art. It has surprisingly been found that shaped catalyst bodies having the desired properties can be produced in an inexpensive way by means of suitable extrusion processes and suitable binders and amounts of binder.

Shaped catalyst bodies based on extruded copper-containing materials are known in principle from the literature.

Thus, Müller et al. in Journal of Catalysis, 218, 2003, pp. 419-426, describe the production of copper oxide/zinc oxide catalyst extrudates having aluminum oxide hydrate as binder material which is present as gamma-aluminum oxide in the finished catalyst. Zinc-free catalysts which are advantageous for the applications described here are not described there. A disadvantage of these extrudates is their significantly reduced active surface area compared to comparative systems which have not been extruded. In addition, the active composition of the catalyst (CuO/ZnO) in the type of extrudate described is diluted by the binder ($Al_2O_3$) which can additionally reduce the activity.

In Example 22 of WO 97/34694, the production of catalyst extrudates from a coprecipitated $CuO/Al_2O_3$ powder without any further additive is described. However, the mechanical stability of the shaped body achieved and the porosity are not completely satisfactory. The porosity achieved in the examples corresponds only to that of tableted material.

It is therefore an object of the invention to provide a catalyst which is simple to produce and has a high mechanical stability and a good catalytic activity, especially for the hydrogenation of carbonyl compounds.

It has now been found that a shaped catalyst body comprising, as active components, copper oxide and an oxidic support material and in addition an oxidic binder matched to the support material, preferably in the form of an extrudate, is easy to produce in industry and also leads to high activities and selectivities and to a high stability.

The invention provides a shaped catalyst body, preferably in the form of an extrudate, which comprises from 5 to 85% by weight of copper oxide and the same oxidic support material in the active composition and as binder.

The catalyst of the invention comprises, as active component, copper oxide, if appropriate in reduced form, and an oxidic support material selected from the group consisting of aluminum oxide, titanium oxide, zirconium oxide, silicon dioxide, the manganese oxides and mixtures thereof. As support material, preference is given to using aluminum oxide which is, in particular, present as X-ray-amorphous oxide in the catalyst. The catalyst can optionally contain one or more further metals or compounds thereof, preferably oxides, from groups 1 to 14 (IA to VIIIA and IB to IVB of the old IUPAC nomenclature) of the Periodic Table of the Elements in proportions of up to 20% by weight, preferably up to 10% by weight. If zinc oxide is present as optional further metal in the catalyst, the proportion of zinc oxide is preferably <5% by weight, particularly preferably <1% by weight and in particular <500 ppm.

In place of the oxides themselves, the active component can also comprise, partly or in its entirety, suitable precursor compounds of copper oxide and the oxidic support material, for example in the form of oxide hydrates, hydroxides and/or carbonates. The copper oxide is preferably present as an intimate mixture with the oxidic support material in the active component.

The proportion of copper oxide or the precursor compounds of copper oxide in the active component is from >10 to 98% by weight, preferably from 30 to 95% by weight, particularly preferably from 50 to 95% by weight and in particular from 80 to 90% by weight (calculated in the ignited state, i.e. based on active component present to an extent of 100% as metal oxide).

The catalyst of the present invention further comprises at least one binder. The binder comprises the same oxidic support material which is also present in the active component, or preferably a precursor of this support material. If the active component comprises copper oxide together with, for example, mainly aluminum oxide or precursors thereof, then the binder likewise comprises alminum oxide and/or precursors thereof, in particular aluminum oxide hydrates, particularly preferably boehmite or pseudoboehmite. If the active component comprises copper oxide together with, for example, mainly silicon oxide or precursors thereof, then the binder likewise comprises silicon oxide and/or precursors thereof, in particular silicic acids, silicic esters or esters of alkylated silicic acids. The embodiment of the catalyst of the invention in which aluminum oxide and/or aluminum oxide precursors are present as constituents both in the active component and in the binder is preferred.

The proportion of copper oxide based on the total mass of the catalyst is from 5 to 85% by weight, preferably from 10 to 70% by weight, particularly preferably from 40 to 65% by weight.

The catalyst of the present invention is in the form of an extrudate. Apart from the abovementioned components, further components and auxiliaries are typically added to the mixture to be extruded. Water and, if appropriate, acids or bases are usually employed. In addition, organic and inorganic substances which contribute to improved processing during extrusion of the catalyst and/or to a further increase in the mechanical strength and/or the desired porosity of the shaped catalyst bodies can additionally be employed as auxiliaries. Such auxiliaries are known to those skilled in the art, and examples include graphite, stearic acid, silica gel, siloxanes, cellulose compounds, starch, polyolefins, carbohydrates (sugars), waxes and alginates.

The further metals or compounds thereof, preferably oxides, from groups 1 to 14 (IA to VIIIA and IB to IVB of the old IUPAC nomenclature) of the Periodic Table which may optionally be present in the catalyst can be present in the active composition and/or in the binder and/or be added as further component to the mixture to be extruded.

In the case of the preferred use of boehmite as binder, aqueous acids, in particular formic acid or nitric acid, are mixed into the mixture being extruded, in addition to, if appropriate, carboxymethylcellulose, potato starch or stearic acid.

Of the oxidic support material present in the catalyst extrudate, i.e. the materials selected from the group consisting of aluminum oxide, titanium oxide, zirconium oxide, silicon dioxide, the manganese oxides and mixtures thereof, from 10 to 98% by weight, preferably from 15 to 95% by weight and in particular from 20 to 50% by weight, comes from the binder used. Correspondingly, from 2 to 90% by weight, preferably from 5 to 85% by weight and particularly preferably from 50 to 80% by weight, of the support material present in the extrudate comes from the active component (in each case calculated as oxidic support material).

The ratios of active composition and binder to be used in the extrusion are determined by the composition of active composition and binder, the target composition of the catalyst or the desired proportion of support material which is to result from the binder.

The choice of an active component having a preferably high proportion of copper oxide and use of a minimum amount of binder comprising the same support material as the active component make it possible to obtain simultaneously very active and extremely mechanically stable extrudates. The production method according to the invention avoids the disadvantageous dilution of the catalyst by a binder component which is inert in the reaction and also achieves a high strength by means of the suitable binder component.

The active compositions can be produced by methods known to those skilled in the art. Preference is given to processes in which the copper oxide is obtained in finely disperse form intimately mixed with the other constituents of the active composition and the acidic oxide. Particular preference is given to precipitating the appropriate metal salts and/or hydroxides from aqueous solution, washing the precipitate and drying and calcining it. Possible metal salts are, for example, nitrates, sulfates, carbonates, chlorides, acetates or oxalates. This starting material is subsequently processed by know methods to produce the shaped bodies by extrusion, if appropriate with addition of auxiliaries.

The extrudates are obtained, for example, by kneading or pan-milling of the starting compounds with the binder, for example boehmite or p-boehmite (AlOOH), and subsequently calcined. The binder can be pretreated prior to extrusion. This is preferably carried out by means of acid, for example formic acid or nitric acid. Other auxiliaries, for example pore formers such as carboxymethylcellulose, potato starch or stearic acid, can be additionally added prior to or during extrusion.

The catalysts of the invention can be produced in various extrudate shapes. Examples which may be mentioned are cylindrical extrudates, star or ribbed extrudates, trilobes, hollow extrudates and honeycombs. The typical diameters of these extrudates are from 0.5 to 10 mm, preferably from 1 to 6 mm, particularly preferably from 1.5 to 3 mm. The mean ratio of length to diameter is from 0.2:1 to 20:1, preferably from 0.7:1 to 10:1, particularly preferably from 1:1 to 5:1.

After shaping, the catalysts are dried and if appropriate calcined. In the case of the preferred catalysts based on copper oxide and aluminum oxide, preference is given to selecting calcination conditions which result in the aluminum oxide being predominantly present in X-ray-amorphous form and the copper oxide being present as finely crystalline tenorite. It is preferred that only <30% by weight, particularly preferably <20% by weight and in particular <10% by weight, of the aluminum oxide is detectable as a crystalline phase in the powder diffraction pattern. The usual calcination temperatures for these preferred catalysts are from 300 to 800° C., preferably from 500 to 700° C. and particularly preferably from 550 to 650° C., at calcination times of from 5 minutes to 5 hours, preferably from 10 minutes to 2 hours.

The BET surface area of the copper catalysts in the oxidic state is from 10 to 400 $m^2/g$, preferably from 15 to 200 $m^2/g$, in particular from 20 to 150 $m^2/g$. The copper surface area ($N_2O$ decomposition) of the reduced catalyst in the installed state is >1 $m^2/g$, preferably >3 $m^2/g$, in particular >6 $m^2/g$, of copper.

The catalyst of the invention has a macroscopically uniform structure. Its components, i.e. the copper oxide, the oxidic support material and the binder, are present as an intimate mixture with one another, as a result of which the catalyst has no large regions (in the mm range) of constituents having a different structure, as is the case, for example, in coated catalysts.

On the microscopic level, on the other hand, the support material is, in a preferred embodiment of the invention, present both as a fine dispersion in the active composition and also in particulate form resulting from the binder added. In this particular embodiment, from 1 to 95%, preferably from 3 to 80% and in particular from 5 to 50%, of the volume of the shaped catalyst body is made up by support particles, i.e. particles having a diameter greater than about 2 μm or a volume greater than about 4 $μm^3$.

In a preferred variant of the invention, shaped catalyst bodies having a defined porosity in the range of large mesopores or small macropores are used. These catalysts have a pore volume of >0.15 ml/g, preferably >0.20 ml/g, particularly preferably >0.30 ml/g, for pore diameters in the range from 10 nm to 100 nm.

A particular embodiment of the present invention therefore provides a shaped catalyst body comprising from 5 to 85% by weight of copper oxide and an oxidic support material, wherein
  a) the shaped body has a pore volume of >0.15 ml/g in the pore diameter range from 10 nm to 100 nm and/or
  b) the oxidic support material in the shaped body is present both in finely disperse form and also to a proportion by volume of from 1 to 95% by volume of the shaped body in particulate form.

The catalyst of the invention preferably has both the pore volume according to feature a) above and the structure of the support material according to feature b).

The porosities specified were determined by mercury intrusion in accordance with DIN 66133. The data in the pore diameter range from 4 nm to 300 nm were evaluated. The porosity according to the invention can be set by methods known to those skilled in the art, for example by a choice of the particle size distribution of active component and, in particular, that of the binder, by means of the parameters of the shaping process and/or by means of the type and amount of additives and auxiliaries used.

When employed as hydrogenation catalyst for carbonyl compounds, the catalyst is used in reduced, activated form. Activation is carried out using reducing gases, preferably hydrogen or hydrogen/inert gas mixtures, either before or after installation in the reactors in which the process of the invention is carried out. If the catalyst is installed in the reactor in oxidic form, activation can be carried out either before the plant is started up for the hydrogenation according to the invention or during start-up, i.e. in situ. Separate activation prior to start-up of the plant is generally carried out using reducing gases, preferably hydrogen or hydrogen/inert gas mixtures, at elevated temperatures, preferably in the range from 100 to 350° C. In the case of in-situ activation, the activation occurs as a result of contact with hydrogen at elevated temperature during running-up of the plant.

The catalyst of the invention is suitable for the hydrogenation of carbonyl compounds, e.g. aldehydes and ketones, to form the corresponding alcohols, with preference being given to aliphatic and cycloaliphatic saturated and unsaturated carbonyl compounds. In the case of aromatic carbonyl compounds, formation of undesirable by-products can occur as a result of hydrogenation of the aromatic ring. The carbonyl compounds can bear further functional groups such as hydroxy or amino groups. Unsaturated carbonyl compounds are generally hydrogenated to the corresponding saturated alcohols. The term "carbonyl compounds" as used for the purposes of the invention encompasses all compounds which have a C=O group, including carboxylic acids and their derivatives. Of course, mixtures of two or more carbonyl compounds can also be hydrogenated jointly. Furthermore, the individual carbonyl compound to be hydrogenated can contain more than one carbonyl group.

The catalyst of the invention is preferably used for the hydrogenation of aliphatic aldehydes, hydroxyaldehydes, ketones, acids, esters, anhydrides, lactones and sugars.

Preferred aliphatic aldehydes are branched and unbranched saturated and/or unsaturated aliphatic $C_2$-$C_{30}$-aldehydes as are obtainable, for example, by the oxo process from linear or branched olefins having internal or terminal double bonds. Furthermore, oligomeric compounds containing more than 30 carbonyl groups can also be hydrogenated.

Examples of aliphatic aldehydes are:

formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylic aldehyde, decyl aldehyde, glutaraldehyde.

Apart from the abovementioned short-chain aldehydes, further suitable aldehydes also include, in particular, long-chain aliphatic aldehydes as can be obtained, for example, by the oxo process from linear a-olefins.

Particular preference is given to enalization products, e.g. 2-ethylhexenal, 2-methylpentenal, 2,4-diethyloctenal or 2,4-dimethylheptenal.

Preferred hydroxyaldehydes are $C_3$-$C_{12}$-hydroxyaldehydes as can be obtained, for example, by aldol reaction of aliphatic and cycloaliphatic aldehydes and ketones with themselves or with formaldehyde. Examples are 3-hydroxypropanal, dimethylolethanal, trimethylolethanal (pentaerythrital), 3-hydroxybutanal (acetaldol), 3-hydroxy-2-ethylhexanal (butyl aldol), 3-hydroxy-2-methylpentanal (propyl aldol), 2-methylolpropanal, 2,2-dimethylolpropanal, 3-hydroxy-2-methylbutanal, 3-hydroxypentanal, 2-methylolbutanal, 2,2-dimethylolbutanal, hydroxypivalaldehyde. Particular preference is given to hydroxypivalaldehyde (HPA) and dimethylolbutanal (DMB).

Preferred ketones are acetone, butanone, 2-pentanone, 3-pentanone, 2-hexanone, 3-hexanone, cyclohexanone, isophorone, methyl isobutyl ketone, mesityl oxide, acetophenone, propiophenone, benzophenone, benzalacetone, dibenzalacetone, benzalacetophenone; 2,3-butanedione, 2,4-pentanedione, 2,5-hexanedione and 5-methyl vinyl ketone.

Furthermore, carboxylic acids and derivatives thereof, preferably those having 1-20 carbon atoms, can be reacted. Particular mention may be made of the following: carboxylic acid such as formic acid, acetic acid, propionic acid, butyric acid, isobutyric acid, n-valeric acid, trimethylacetic acid ("pivalic acid"), caproic acid, enanthic acid, caprylic acid, capric acid, lauric acid, myristic acid, palmitic acid, stearic acid, acrylic acid, methacrylic acid, oleic acid, elaidic acid, linoleic acid, linolenic acid, cyclohexane-carboxylic acid, benzoic acid, phenylacetic acid, o-toluic acid, m-toluic acid, p-toluic acid, o-chlorobenzoic acid, p-chlorobenzoic acid, o-nitrobenzoic acid, p-nitrobenzoic acid, salicylic acid, p-hydroxybenzoic acid, anthranilic acid, p-aminobenzoic acid, oxalic acid, maleic acid, succinic acid, glutaric acid, adipic acid, pimelic acid, suberic acid, azelaic acid, sebacic acid, maleic acid, fumaric acid, phthalic acid, isophthalic acid, terephthalic acid;

carboxylic esters such as the $C_1$-$C_{10}$-alkyl esters of the abovementioned carboxylic acids, in particular methyl formate, ethyl acetate, butyl butyrate, dimethyl terephthalate, dimethyl adipate, dimethyl maleate, methyl (meth)acrylate, butyrolactone, caprolactone, and polycarboxylic esters such as esters of polyacrylic and polymethacrylic acids and their copolymers and polyesters such as polymethyl methacrylate, terephthalic esters and other industrial plastics;

fats;

carboxylic anhydrides such as the anhydrides of the abovementioned carboxylic acids, in particular acetic anhydride, propionic anhydride, benzoic anhydride and maleic anhydride, carboxamides such as formamide, acetamide, propionamide, stearamide, terephthalamide.

It is also possible to react hydrocarboxylic acids such as lactic, malic, tartaric or citric acid, or amino acids such as glycine, alanine, proline and arginine, and peptides.

The process of the invention is particularly preferably used for the hydrogenation of esters, anhydrides, aldehydes and hydroxyaldehydes.

The carbonyl compound to be hydrogenated can be fed into the hydrogenation reactor either alone or as a mixture with the product of the hydrogenation reaction, with this being able to occur in undiluted form or using an additional solvent. Suitable additional solvents are, in particular, water, alcohols such as methanol, ethanol and the alcohol formed under the reaction conditions. Preferred solvents are water, THF, NMP and also ethers such as dimethyl ether, diethyl ether, MTBE, particularly preferably water.

The hydrogenation of starting materials which are liquid under the reaction conditions can be carried out either in the upflow mode or in the downflow mode, in each case preferably with circulation, generally at a temperature of from 50 to 250° C., preferably from 70 to 200° C., particularly preferably from 100 to 140° C., and a pressure of from 15 to 250 bar, preferably from 20 to 200 bar, particularly preferably from 25 to 100 bar. Gas-phase hydrogenations are usually carried out at temperatures of from 120 to 350° C., preferably from 180 to 300° C., and a pressure of from 1 to 100 bar, preferably from 1 to 60 bar and in particular from 2 to 20 bar.

The catalysts used according to the invention generally have a satisfactory operating life. Should the activity and/or selectivity of the catalyst nevertheless drop over the course of its period of operation, it can be regenerated using measures known to those skilled in the art. Among these, preference is given to reductive treatment of the catalyst in a stream of hydrogen at elevated temperature. If appropriate, the reductive treatment can be preceded by an oxidative treatment. In this case, a gas mixture comprising molecular oxygen, for example air, is passed at elevated temperature through the catalyst bed. A further possibility is to rinse the catalysts with suitable solvents.

The hydrogenation process using the according to the invention achieves high conversions and selectivities, and the catalysts display a high chemical stability in the presence of the reaction mixture. The catalysts produced according to the invention have a significantly increased mechanical stability both in the oxidic state and in the reduced state, as a result of which the process of the invention is particularly economical.

The invention is illustrated by the following examples.

Measurement of the BET Surface Area

The determination of the BET surface areas was carried out by adsorption of $N_2$ in accordance with DIN 66131.

Measurement of the Cutting Hardness

The measurement of the cutting hardness was carried out as follows:

25 visually crack-free extrudates chosen at random are tested in succession by pressing a cutter having a thickness of 0.3 mm onto the respective extrudate with increasing force until the extrudate is cut through. The force required for this is the cutting hardness in N.

EXAMPLE 1

Preparation of an Active Composition According to the Invention 1.5 l of water are placed in a heatable precipitation vessel equipped with an agitator and heated to 80° C. A metal salt solution comprising 877 g of $Cu(NO_3)_2 * 2.5H_2O$ and 551 g of $Al(NO_3)_3 * 9H_2O$ in 2000 ml of water and a sodium carbonate solution (20% strength by weight) are metered simultaneously into this precipitation vessel over a period of one hour while stirring. The sodium carbonate solution is metered in in such an amount that a pH of 6 is established in the precipitation vessel. After all the metal salt solution has been added, further sodium carbonate solution is metered in until the pH in the precipitation vessel is 8 and the mixture is stirred at this pH for a further 15 minutes. The total consumption of sodium carbonate solution is 3.7 kg. The suspension formed is filtered and the solid is washed with water until the washings no longer contain nitrate (<25 ppm). The product is dried at about 120° C. The active composition prepared in this way comprises, calculated as oxides, about 80% by weight of CuO and 20% by weight of $Al_2O_3$.

Production of the Extrudates 133 g of boehmite (Versal 250, from Sasol) is treated with formic acid (30% strength by weight) in a Mix-Muller, mixed with the dried active composition and, after addition of 233 ml of water, intensively mixed. The compounded mass is subsequently extruded to form extrudates having a diameter of 2 mm and a mean length of 8 mm. The extrudates are subsequently dried at about 120° C. and calcined at 600° C. The catalyst extrudates comprise, calculated as oxide, about 65% by weight of CuO and 35% by weight of $Al_2O_3$. About 54% of the oxidic support material $Al_2O_3$ in the catalyst comes from the binder.

The most important catalyst properties are summarized in Table 2.

Hydrogenation of Maleic Anhydride (MA) to Give Mixtures of Tetrahydrofuran (THF) and Gamma-Butyrolactone (GBL) Over the Catalyst of the Invention Before commencement of the reaction, the catalyst is subjected to a treatment with hydrogen. For this purpose, the reactor is heated to 180° C. and the catalyst is reduced for the time indicated in Table 1 by means of the mixture of hydrogen and nitrogen indicated in each case at atmospheric pressure.

TABLE 1

| Time (minutes) | Hydrogen (standard l/h) | Nitrogen (standard l/h) |
|---|---|---|
| 120 | 50 | 950 |
| 30 | 100 | 900 |
| 30 | 500 | 500 |

The catalyst is subsequently treated with 200 standard l/h of hydrogen at 280° C. for 1 hour.

To carry out the hydrogenation, molten MA is pumped in countercurrent into a vaporizer which is operated at 245° C. and through which hydrogen flows. The gas stream of hydrogen and MA is fed into the heated reactor (diameter: 27 mm) charged with a mixture of 70 ml of catalyst and 70 ml of glass rings; the gaseous output from the reactor is quantitatively analyzed by gas chromatography. The operating parameters and experimental results are shown in Table 3.

EXAMPLE 2

Preparation of an Active Composition According to the Invention 1.5 l of water are placed in a heatable precipitation vessel equipped with an agitator and heated to 80° C. A metal salt solution comprising 877 g of $Cu(NO_3)_2 * 2.5H_2O$ and 1410 g of $Al(NO_3)_3 * 9H_2O$ in 2000 ml of water and a sodium carbonate solution (20% strength by weight) are metered simultaneously into this precipitation vessel over a period of one hour while stirring. The sodium carbonate solution is metered in in such an amount that a pH of 6 is established in the precipitation vessel. After all the metal salt solution has been added, further sodium carbonate solution is metered in until the pH in the precipitation vessel is 8 and the mixture is stirred at this pH for a further 15 minutes. The total consumption of sodium carbonate solution is 4.4 kg. The suspension formed is filtered and the solid is washed with water until the washings no longer contain nitrate (<25 ppm). The product is dried at about 120° C. The active composition prepared in this way comprises, calculated as oxides, about 61% by weight of CuO and 39% by weight of $Al_2O_3$.

Production of the Extrudates 160 g of boehmite (Versal 250, from Sasol) is treated with formic acid (30% strength by weight) in a Mix-Muller, mixed with the dried active composition and, after addition of 327 ml of water, intensively mixed. The compounded mass is subsequently extruded to form extrudates having a diameter of 2 mm and a mean length of 8 mm. The extrudates are subsequently dried at about 120° C. and calcined at 600° C. The catalyst extrudates comprise, calculated as oxide, about 50% by weight of CuO and 50% by weight of $Al_2O_3$. About 36% of the oxidic support material $Al_2O_3$ in the catalyst comes from the binder.

The most important catalyst properties are summarized in Table 2. The results of a hydrogenation experiment corresponding to Example 1 are shown in Table 3, and an electron micrograph of the catalyst extrudate after reduction and reoxidation is shown in FIG. 1.

COMPARATIVE EXAMPLE 1

Production of the Extrudates 88.7 g of boehmite (Versal 250, from Sasol) is treated with formic acid (30% strength by weight) in a Mix-Muller, mixed with 83.4 g of basic copper carbonate (malachite; $CuCO3*Cu(OH)2$; from Aldrich) and, after addition of 80 ml of water, intensively mixed. The compounded mass is subsequently extruded to form extrudates having a diameter of 2 mm and a mean length of 8 mm. The extrudates are subsequently dried at about 120° C. and calcined at 600° C. The extrudates comprise 50% by weight of CuO and 50% by weight of $Al_2O_3$. In this example, the active composition contains no support component; the support thus comes exclusively from the binder used.

The most important catalyst properties are summarized in Table 2. The results of a hydrogenation experiment using the noninventive catalyst C1 and carried out in a manner analogous to example 1 are shown in Table 3.

TABLE 2

Catalyst data

| Example | Bulk density [g/l] | Cutting hardness [N] | Diameter [mm] | BET [m2/g] | Pore volume [cm3/g] total | for D = 10-100 nm |
|---|---|---|---|---|---|---|
| 1 | 906 | 25 | 1.7 | 104 | 0.31 | 0.24 |
| 2 | 790 | 20 | 1.7 | 121 | 0.48 | 0.36 |
| C 1 | 620 | 11 | 1.8 | 155 | 0.59 | 0.13 |

TABLE 3

Hydrogenation results

| Ex. | p [bar] | T of hot spot [° C.] | WHSV [kg of MA/l of cat * h] | GHSV [1/h] | c (MA) in the feed [% by volume] | C (MA) [mol %] | S (SA) [mol %] | S (THF) [mol %] | S (GBL) [mol %] | S (BuOH) [mol %] |
|---|---|---|---|---|---|---|---|---|---|---|
| 1 | 10 | 250 | 0.15 | 2800 | 1.25 | 100 | 0.7 | 51.6 | 45.8 | 0.3 |
| 2 | 10 | 250 | 0.17 | 3200 | 1.25 | 100 | 1.5 | 49.3 | 47.6 | 0.1 |
| C 1 | 10 | 250 | 0.03 | 700 | 1.15 | 100 | 60.6 | 1.0 | 32.4 | 0 |

FIG. 1 shows a scanning electron micrograph of a catalyst extrudate as described in example 2 (image produced by the backscattered electrons from a polished section; extract shown in the figure about 170×170 μm$^2$). In the dark regions, virtually only aluminum is detected by means of EPMA (in this scanning electron image, regions of relatively high density, e.g. as a result of a high copper content, appear lighter); in the other regions, both aluminum and copper are present. The areas of the dark particles indicate a proportion of particulate aluminum oxide in this sample of about 18%; assuming that the polished section is representative of the sample, this corresponds to about 18% by volume of particulate $Al_2O_3$ in the total catalyst extrudate.

The invention claimed is:

1. A shaped catalyst body having a macroscopically uniform structure and comprising:
   from 5 to 85% by weight of copper oxide as an active component and
   $Al_2O_3$ as oxidic support material and as binder, wherein
   a) the shaped catalyst body has a pore volume of greater than 0.15 ml/g in the pore diameter range from 10 nm to 100 nm, and
   b) the oxidic support material in the shaped body is present both in finely disperse form and also to a proportion by volume of from 1 to 95% by volume of the shaped body in particulate form and is predominantly present as X-ray-amorphous material.

2. The shaped catalyst body according to claim 1, which is an extrudate.

3. The shaped catalyst body according to claim 2, wherein said extrudate is in the form of a cylindrical extrudate, a star extrudate, a ribbed extrudate, a trilobed extrudate, a hollow extrudate, or a honeycombed extrudate.

4. The shaped catalyst body according to claim 3, wherein the diameter of said extrudate is from 0.5 to 10 mm.

5. The shaped catalyst body according to claim 1, wherein the active component additionally includes aluminum oxide and the oxidic support material additionally includes aluminum oxide.

6. The shaped catalyst body according to claim 1, wherein the shaped body has a pore volume of greater than 0.30 ml/g in the pore diameter range from 10 nm to 100 nm.

7. The shaped catalyst body according to claim 1, wherein a BET surface area of said copper oxide is from 10 to 400 m$^2$/g.

8. The shaped catalyst body according to claim 1, wherein said $Al_2O_3$ is present in an amount ranging from 15 to 95% by weight.

9. The shaped catalyst body according to claim 1, wherein the oxidic support material further comprises at least one of titanium oxide, zirconium oxide, silicon oxide, and manganese oxide.

10. A process for producing a shaped catalyst body according to claim 1, comprising mixing an active component comprising from 10 to 98% by weight of copper oxide and an oxidic support material with a binder comprising the same support material or a precursor thereof and shaping the same to form shaped bodies.

11. The process according to claim 10, wherein from 10 to 98% by weight of the oxidic support material in the catalyst comes from the binder used.

12. A process for the hydrogenation of carbonyl compounds, comprising phase hydrogenating a carbonyl compound in the presence of the shaped catalyst body according to claim 1.

13. A process for gas-phase hydrogenation of maleic anhydride comprising gas-phase hydrogenating maleic anhydride in the presence of the shaped catalyst body according to claim 1.

14. A shaped catalyst body having a macroscopically uniform structure and consisting essentially of:
   a catalytically active composition containing 5 to 85% by weight of copper oxide and $Al_2O_3$ in a fine dispersion, and
   $Al_2O_3$ in particulate form as a binder.

15. The shaped catalyst body according to claim 14, which that has a pore volume of greater than 0.15 ml/g for pore diameters in the range 10 nm to 100 nm.

16. The shaped catalyst body according to claim 15, wherein the binder has a particle size greater than about 2 μm or a particle volume greater than about 4 μm$^3$.

17. The shaped catalyst body according to claim 16, wherein the proportion of the particulate form of $Al_2O_3$ ranges from 1 to 95% by volume.

18. The shaped catalyst body according to claim 17, wherein the particulate proportion of $Al_2O_3$ is predominantly present as X-ray-amorphous material.

19. The shaped catalyst body according to claim 14, which is prepared by a process comprising:

admixing metal salts to form a suspension containing copper oxide and $Al_2O_3$, recovering a catalytically active composition containing CuO and $Al_2O_3$, admixing the catalytically active composition containing CuO and $Al_2O_3$ with a binder that comprises $Al_2O_3$ or precursor thereof, extruding the admixture to form an extrudate, and calcining the extrudate at a temperature ranging from 300° C. to 800° C.

20. The shaped catalyst body according to claim 19, comprising admixing the catalytically active composition containing CuO and $Al_2O_3$ with a boehmite binder.

\* \* \* \* \*